(12) United States Patent
O'Lenick

(10) Patent No.: US 8,808,677 B1
(45) Date of Patent: *Aug. 19, 2014

(54) GLYCERIN POLYESTERS WITH TERMINAL MODIFICATION

(71) Applicant: Thomas George O'Lenick, Dacula, GA (US)

(72) Inventor: Thomas George O'Lenick, Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/998,740

(22) Filed: Dec. 2, 2013

Related U.S. Application Data

(63) Continuation-in-part of application No. 13/986,052, filed on Mar. 28, 2013, now Pat. No. 8,636,991, which is a continuation-in-part of application No. 13/373,974, filed on Dec. 8, 2011, now Pat. No. 8,496,918.

(51) Int. Cl.
| | |
|---|---|
| *A61Q 5/12* | (2006.01) |
| *C07F 7/08* | (2006.01) |
| *A61K 8/85* | (2006.01) |
| *A61Q 19/00* | (2006.01) |

(52) U.S. Cl.
CPC .. *A61K 8/85* (2013.01); *A61Q 19/00* (2013.01)
USPC .......................................... 424/70.12; 554/77

(58) Field of Classification Search
None
See application file for complete search history.

(56) References Cited

U.S. PATENT DOCUMENTS 6,306,906 B1 * 10/2001 Wohlman et al. ............. 514/552

* cited by examiner

*Primary Examiner* — Bethany Barham
*Assistant Examiner* — Danah Al-Awadi

(57) ABSTRACT

The present invention is directed to a series of functionalized glycerin based polymers that have been designed to have very specific substitution patterns, herein referred to as regio-specific substitution (RSS). We have surprisingly found that by linking triglycerides into polymer backbones and controlling the location of the different alkyl groups along that backbone, the performance and structure can be fine tuned. The properties of these polymers can be controlled and tuned by judicial control of the polymerization conditions, specifically by employing the use of mono-functional monomers. This polymer will has "compartments" of solid and liquid pendant group domains if the proper pendant groups are chosen. This unique multi-dimensional, high definition polymer will have very unique physical properties, including unique shear and flow behaviors. These polymers will provide outstanding and unique skin feels when used in cosmetic applications.

19 Claims, No Drawings

GLYCERIN POLYESTERS WITH TERMINAL MODIFICATION

RELATED APPLICATION

This application is a continuation in part of co-pending U.S. Ser. No. 13/986,052 filed Mar. 28, 2013, which is in turn a continuation in part of U.S. Ser. No. 13/373,974, filed Dec. 8, 2011.

FIELD OF THE INVENTION

The present invention is directed to a series of functionalized glycerin based polymers that have been designed to have very specific substitution patterns, herein referred to as regiospecific substitution (RSS). Natural oils are triglycerides produced by plants and animals as a mechanism to store energy in the form of neutral fats. While being very successful as a store of energy for cells, these products are oily and do not possess the derived aesthetics for widespread use in cosmetics. The compounds of the present invention provide properties including skin feel and thermo-sensitive properties (i.e. alteration in properties as the temperature increases). The properties of the natural triglycerides are controlled by the fatty (alkyl) group contained therein and normally are predominantly oleyl groups (C18). Nature does not provide much of a variation in the groups. We have surprisingly found that by linking triglycerides into polymer backbones and controlling the location of the different alkyl groups along that backbone, the performance and structure can be fine tuned. To improve the performance and properties of triglycerides, several polymeric triglyceride mimics were synthesized. The properties of these polymers can be controlled and tuned by judicial control of the polymerization conditions, specifically by employing the use of mono-functional monomers. This polymer will has "compartments" of solid and liquid pendant group domains if the proper pendant groups are chosen. This unique multi-dimensional, high definition polymer will have very unique physical properties, including unique shear and flow behaviors. These polymers will provide outstanding and unique skin feels when used in cosmetic applications.

BACKGROUND OF THE INVENTION

Triglycerides are common natural materials, their structure is:

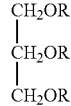

Triglycerides are esters that are the reaction product of glycerin and fatty acids.

Triglycerides are very common in nature and are commonly used in cosmetic products to provide physical properties and ascetics. Triglycerides are commonly called oils, fats, butters and waxes. These terms are used to describe the physical and chemical composition of the triglyceride. Butters, oils and fats are all triglycerides. The major physical difference between butters, oils and fats are their melt and titer points: Fats have a titer point of over 40.5° C., oils have a titer point of below 40.5° C., and butters have a titer below 40.5° C. but above 20° C. Oils are liquid at room temperature and we now use this word to describe any compound that is a liquid and is insoluble in water. As a result, Jojoba is referred to as oil, despite the fact it is really a liquid wax.

Because oils, fats, butters and waxes are complex mixtures of homologues of similar chemical structures, it is difficult to obtain a true melting point. As the lower molecular weight fractions melt, they act as solvents to dissolve the higher molecular weight products. This results in a very wide melting "range" for these compounds. For this reason, titer point is generally determined on fats, oils, waxes and butters.

Titer is defined as the re-solidification point of the melted oil, fat butter or wax. The procedure is to heat the product to be tested until it is completely liquid, then to slowly cool with stirring. This is done until the temperature stays constant for 30 seconds, or begins to rise. The titer point is the highest temperature indicated by this rise.

Triglycerides are the tri-ester of glycerin with three equivalents of fatty acid. Fatty acids are defined as those acids having alkyl or alkylene groups being C-5 and higher. The reaction is as follows:

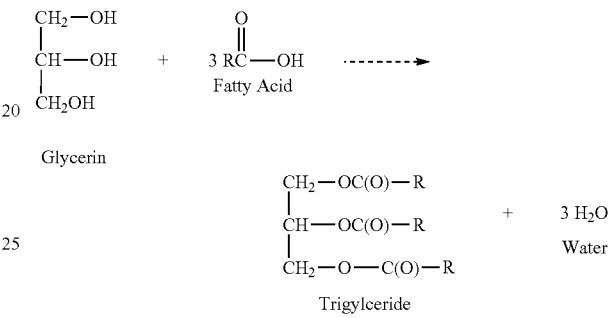

Triglycerides occur commonly in nature, but lack the desired aesthetics for many personal care applications. It is the pursuit of improving the feel of these commonly occurring natural triglycerides that are the materials of interest in the present invention.

U.S. Pat. No. 2,914,546 to Barsky et al teaches interesterification of mixed glyceryl compounds.

U.S. Pat. No. 6,306,906 to Wohlman and O'Lenick teach a process for conditioning hair and skin which comprise contacting the skin or hair with an effective conditioning concentration of a of the reaction product of meadowfoam oil and an ester selected from the group consisting of beeswax, jojoba oil, carnauba wax, and candelilla wax.

U.S. Pat. No. 6,180,668 to Wohlman and O'Lenick disclose a series of "reconstituted meadowfoam oils", used on skin for moisturizing and emollient applications. The term reconstituted as used hereon refers to a process in which meadowfoam oil and one or more oils of natural origin are transesterified under conditions of high temperature and catalyst to make a "reconstituted product" having an altered alkyl distribution and consequently altered chemical and physical properties.

These above listed patents are all incorporated herein by reference.

None of these patents provide polyester derivatives of mixed fatty esters of glyceryl as envisioned by the present invention. Nor do they provide any regiospecificity, that is a difference between $R^1$ and $R^4$ that is easily controlled by the reaction sequence. Finally, no ester has included silicone in the structure along with the other improvements lacking in the compounds existing before the current molecules. The result is the materials heretofore known are not polymeric materials that have the benefit of unique physical properties due to molecular weight increase, no skin penetration due to high molecular weight, and the combination of liquid and solid domain groups critical to the properties of the present invention. Furthermore, the incorporation of the silicone monomer allows for a unique solubility of the polymer. This unique solubility leads to superior surface activity when compared to their organic (carbon containing) counterparts.

Fatty acids of differing chain lengths and structures will have different physical properties. A triglyceride containing two different fatty chain length with have physical properties of a blend of the two fatty acids. If the fatty acids are confined to a domain of the polymer (pendant groups are located in regio-specific positions of the polymer backbone), a multi-domain polymer is formed. This multi-domain polymer will have highly organized "pockets" or domains of solid fatty groups, surrounded by liquid domains. The physical properties of the multi-domain polymer will be extremely different than the random triglyceride. By judicious control of the placement of these domains results in a high definition polymer. The preparation of polymers with highly desired aesthetics requires that different sections of the molecule have controlled alkyl groups. Addition of all the groups in the reaction mixture results in a random alkyl substitution pattern and loss of the desired aesthetics. Only by careful stepwise reaction can the products having exact structural properties be assured, thereby assuring performance in highly sophisticated formulations.

DETAILED DESCRIPTION OF THE INVENTION

The present invention is aimed at a series of novel glycerin polyesters that provide desired aesthetics and structure in cosmetic formulation. These glycerin polymers are synthesized by polycondensation polymerization, in the presence of a monofunctional monomer or terminal group. By carefully choosing the groups the properties can be dramatically altered. The mono-functional alcohols, being only able to react in one position, can only be located on the polymer chain ends. This provides very unique polymer structure and morphology. These regiospecific polyesters will have very unique physical properties and have a wide variety of solubilities. Furthermore, by the incorporation of a co-monomer will produce a copolymer with drastically different solubilities and aesthetics.

SUMMARY OF THE INVENTION

It has been discovered that not only the polymer make up, i.e. the monomers that make up the polymer backbone, but also the polymer design can be controlled and used as an efficient tool in tuning the ascetics and performance of a polymer. The polymers of the current invention are synthesized by a step growth polymerization, specifically a polycondensation polymerization. A simple example of a polycondensation polymerization is shown below:

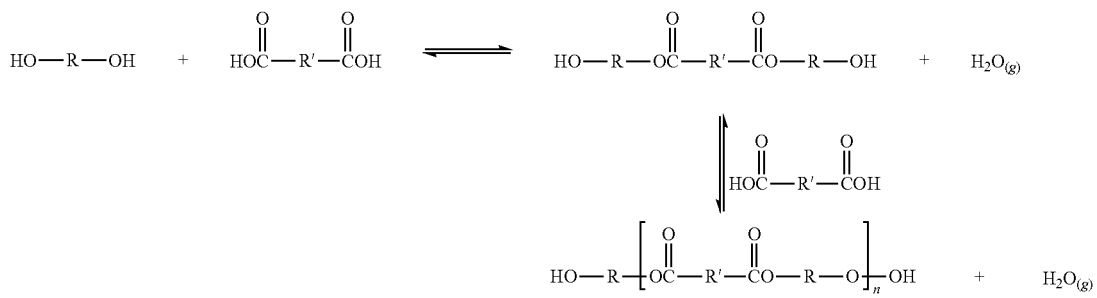

In this simple example, the polymerization is the reaction between a di-acid and a di-alcohol. The polymerization is an equilibrium reaction that gives off water as a byproduct. The polymerization proceeds to high molecular weight by the removal of water as steam. It is common practice in polymer chemistry to actively control the molecular weight of the polymer by controllable techniques. One of these techniques is the use of mono-functional monomers during the polymerization process. Mono-functional monomers or so-called "chain terminators", will react during the polymerization process like every other monomer. The major difference between a mono-functional monomer and a multifunctional monomer is that unlike a typical multifunctional monomer, a mono-functional monomer has only one reactive group. The moment that the mono-functional monomer reacts onto the polymer backbone the polymer chain loses the ability to continue to grow because it has no more react-able functional groups. The chain terminator reaction is as follows:

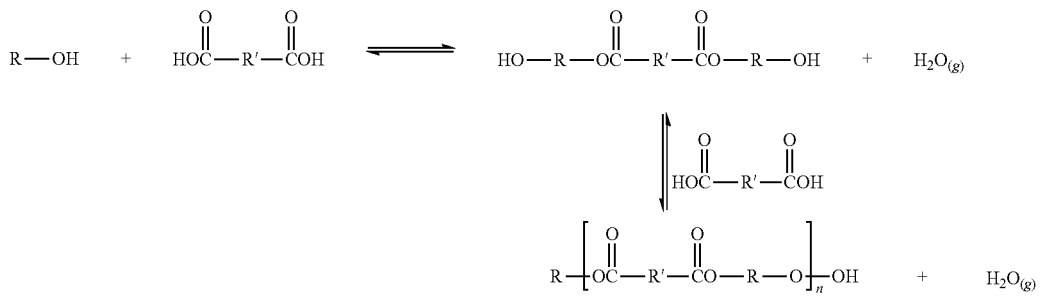

Chain terminators get their names because once they react, the polymerization stops so they are always on the end of the polymer chain.

We have found that by the use of mono-functional monomers can be used to design a polymer that is regospecific, (also refereed to as regio-specific substitution (RSS)).

Regiospecific refers to a polymer that has regions of different pendant groups. A polymer can be synthesized that has two or more regions by utilizing mono-functional monomers. The polymer chain ends are controlled by the use of mono-functional monomers, while the internal pendant groups can be reacted onto the polymer backbone by the use of a different fatty acid. The regions of the polymer are shown below:

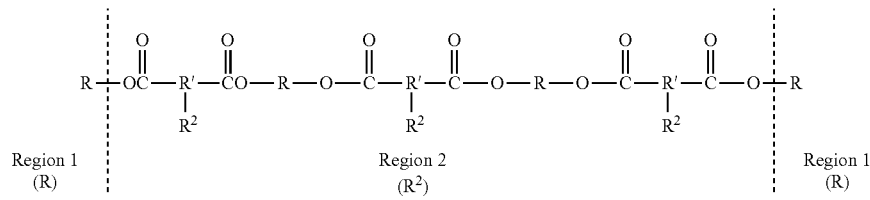

Region 1 (R)     Region 2 ($R^2$)     Region 1 (R)

As shown above, the polymer's pendant groups can be controllably placed into two different regions. These regions will then allow the polymer to act like a block copolymer. Regiospecific polymers will have drastically different properties, i.e. different melt point, crystallinity, and solubility than the same polymer made in a random approach.

This regiospecific polymer is obtained by the multi-step polymerization approach. In the first step a try functional alcohol is reacted with a di-acid and a mono-functional acid as shown below:

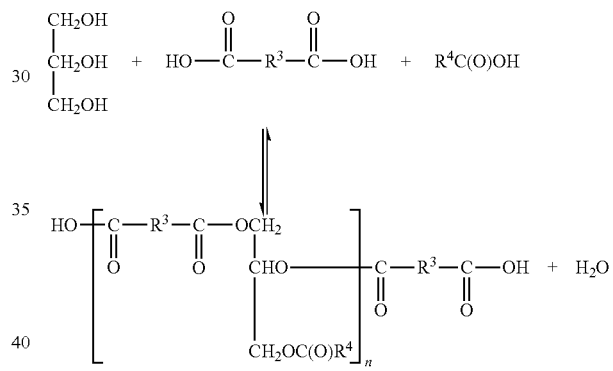

As seen above, the polymerization occurs as a typical polycondensation polymerization. The polymerization will proceed until one of the monomers is completely consumed. Once the polymerization has reached a desired chain length, the polymerization can be terminated by the addition of a "chain terminator". Chain terminators are monofunctional monomers that will react onto the polymer chain end and prevent the polymer from growing. The chain terminator reaction is shown below.

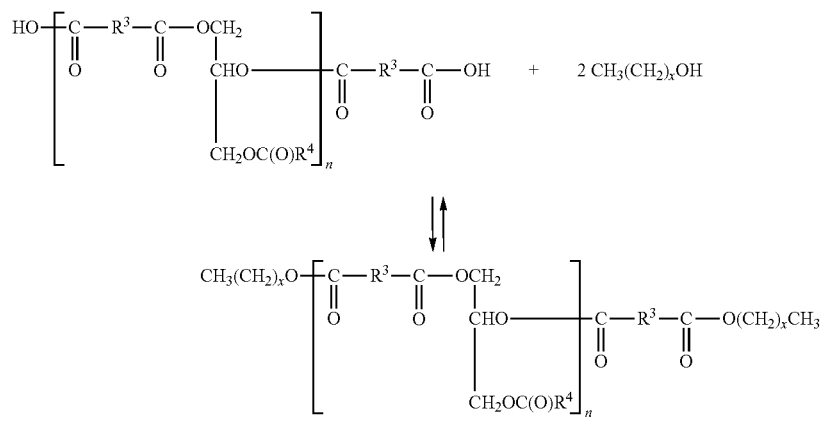

As seen above, once the chain terminators react with the growing polymer chain, the chain loses the ability to continue to react.

This new technique provides a way to selectively add end groups onto the polymer chain ends, and different internal groups, crosslinked with a linear di functional silicone. Since the chain terminators are held until the end of the polymerization, they are protected from trans-esterification reaction with other alcohols involved in the polymerization process. The polymer produced is designed specifically to maximize the performance of the polymers. These polymers are classified as High Definition Polymers. The term "High Definition Polymers" refers to a class of polymers that have specific structures that affect the polymer performance. A glycerin polyester of the current invention that has both a solid and liquid pendant and terminal groups and will produce a High Definition Polymer that has structured liquid and solid domains.

Glycerin Polyester

A glycerin polyester having the following structure:

$$R^2O-C(O)-R^3-C(O)-[(OR^1O-C(O)-R^3-C(O))_a(OCH_2CHO-C(O)-R^3-C(O)-OR^2)_b]_n$$
$$CH_2OC(O)R^4$$

wherein, a is an integer ranging from 0 to 9;

b is an integer ranging from 1 to 10; with the proviso a+b=n;

n is an integer ranging from 5 to 10;

$R^1$ is alkyl ranging from 3 to 12 carbons;

$R^2$ is independently selected from the group consisting of (a) alkyl having 8 to 26 carbons, (b) alkyl containing 29 to 48 carbons, (c) a branched alkyl having the structure:

$$CH_3-(CH_2)_x-CH((CH_2)_yCH_3)-CH_2-$$

and mixtures thereof;

y is an integer ranging from 3-15;

x is an integer ranging from 5-17;

$R^3$ is independently selected from the group consisting of alkyl having 2 to 12 carbons, a alkyl having the following structures:

[cyclohexane structure with —CH$_2$, (CH$_2$)$_4$CH$_3$, HC=, HC=, (CH$_2$)$_4$CH$_3$, HC—(CH$_2$)$_7$CH$_2$— substituents]

[cyclohexane structure with —CH$_2$, (CH$_2$)$_4$CH$_3$, H$_2$C, H$_2$C, (CH$_2$)$_4$CH$_3$, HC—(CH$_2$)$_7$CH$_2$— substituents]

and mixtures thereof;

$R^4$ is alkyl having 8 to 34 carbon atoms or —(CH$_2$)$_{10}$CH(OH)(CH$_2$)$_5$CH$_3$.

Preferred Embodiment

In a preferred embodiment n is 5.
In a more preferred embodiment a is 0.
In a more preferred embodiment b is 5.
In a more preferred embodiment $R^3$ is

[cyclohexane structure with —CH$_2$, (CH$_2$)$_4$CH$_3$, H$_2$C, H$_2$C, (CH$_2$)$_4$CH$_3$, HC—(CH$_2$)$_7$CH$_2$— substituents]

In a more preferred embodiment $R^3$ is

[cyclohexene structure with —CH$_2$, (CH$_2$)$_4$CH$_3$, HC=, HC=, (CH$_2$)$_4$CH$_3$, HC—(CH$_2$)$_7$CH$_2$— substituents]

In a more preferred embodiment $R^4$ is alkyl containing 10 carbons.

In a more preferred embodiment $R^1$ is alkyl containing 3 carbons.

In a more preferred embodiment $R^2$ is a branched alkyl containing 28 carbons.

Another aspect of the present invention is a process for conditioning skin which comprises contacting the skin with an effective conditioning concentration of a polyester having the following structure:

$$R^2O-C(O)-R^3-C(O)-[(OR^1O-C(O)-R^3-C(O))_a(OCH_2CHO-C(O)-R^3-C(O)-OR^2)_b]_n$$
$$CH_2OC(O)R^4$$

wherein, a is an integer ranging from 0 to 10;

b is an integer ranging from 1 to 10; with the proviso a+b=n;

n is an integer ranging from 5 to 10;

$R^1$ is alkyl ranging from 3 to 12 carbons, or mixtures thereof;
$R^2$ is independently selected from the group consisting of
  (a) alkyl having 8 to 26 carbons,
  (b) alkyl containing 29 to 48 carbons,
  (c) a branched alkyl having the structure:

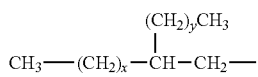

and mixtures thereof;
y is an integer ranging from 3-15;
x is an integer ranging from 5-17;
$R^3$ is independently selected from the group consisting of alkyl having 2 to 12 carbons, a branched alkyl having the following structure:

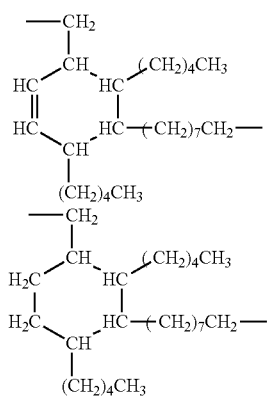

and mixtures thereof;
$R^4$ is alkyl having 8 to 34 carbon atoms or —$(CH_2)_{10}CH(OH)(CH_2)_5CH_3$.

Another aspect of the present invention is a polyester made by the esterification reaction of:
(A) a fatty acid having the structure;

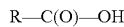

wherein;
R is selected from the group consisting of
  alkyl having 7 to 33 carbon atoms;
  and
  alkylene having 17 to 21 carbon atoms;
(B) a fatty alcohol having the following structure:

wherein:
R' alkyl having 8 to 22 carbon atoms;
(C) a diacid selected from the group consisting of
  (i) dimer acid;
  (ii) hydrogenated dimer acid
  and
  (iii) dicarboxylic acid having following structure;

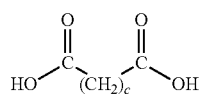

wherein;
c is an integer ranging from 1 to 10.

(D) a guerbet alcohol having the following structure;

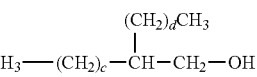

wherein;
d is an integer ranging from 3-15;
c is an integer ranging from 5-17;
(E) a diol having following structure;

$$HO(CH_2)_xOH$$

wherein;
x is an integer ranging from 3 to 12.
and
(F) glycerin having the following structure:

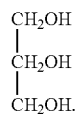

Another aspect of the present invention is a process for conditioning skin which comprises contacting the skin with an effective conditioning concentration of a polyester made by the esterification reaction of:
(A) a fatty acid having the structure;

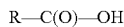

wherein;
R is selected from the group consisting of
  alkyl having 7 to 33 carbon atoms;
  and
  alkylene having 17 to 21 carbon atoms;
(B) a fatty alcohol having the following structure:

wherein:
R' alkyl having 8 to 22 carbon atoms;
(C) a diacid selected from the group consisting of
  (i) dimer acid;
  (ii) hydrogenated dimer acid
  and
  (iii) dicarboxylic acid having following structure;

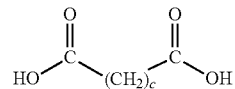

wherein;
c is an integer ranging from 1 to 10.
(D) a guerbet alcohol having the following structure;

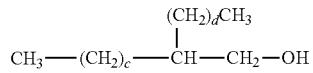

wherein;
d is an integer ranging from 3-15;
c is an integer ranging from 5-17;

(E) a diol having following structure;

HO(CH$_2$)$_x$OH wherein;
x is an integer ranging from 3 to 12.
and
(F) glycerin having the following structure:

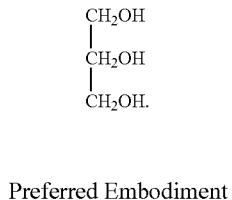

Preferred Embodiment

In a preferred embodiment said effective conditioning concentration ranges from 0.1 to 20% by weight.
In a preferred embodiment, R is alkyl having 7 carbon atoms.
In a preferred embodiment, R is alkyl having 18 carbon atoms.
In a preferred embodiment, c is 4
In a preferred embodiment, c is 10
In a preferred embodiment, x is 12.
In a preferred embodiment, R' is alkyl having 8 carbon atoms.
In a preferred embodiment, R' is alkyl having 12 carbon atoms.

Raw Materials
Fatty Acids

Fatty acids useful in the practice of the present invention are items of commerce commercially available from Cognis.

Fatty Acid Names

Fatty acids useful as raw materials in the preparation of compounds of the present invention are commercially available from a variety of sources including Procter and Gamble of Cincinnati Ohio. The structures are well known to those skilled in the art.

R—C(O)—OH

| Example | R Formula | Common Name | Molecular Weight |
|---|---|---|---|
| | | Saturated | |
| 1 | C$_7$H$_5$ | Caprylic | 144 |
| 2 | C$_9$H$_{19}$ | Capric | 172 |
| 3 | C$_{11}$H$_{23}$ | Lauric | 200 |
| 4 | C$_{13}$H$_{27}$ | Myristic | 228 |
| 5 | C$_{14}$H$_{29}$ | Pentadecanoic | 242 |
| 6 | C$_{15}$H$_{31}$ | Palmitic | 256 |
| 7 | C$_{17}$H$_{35}$ | Stearic | 284 |
| 8 | C$_{17}$H$_{35}$ | Isosteric | 284 |
| 9 | C$_{18}$H$_{36}$O$_3$ | 12-Hydroxystearic | 300 |
| 10 | C$_{21}$H$_{43}$ | Behenic | 340 |
| 12 | C$_{26}$H$_{53}$ | cetrotic | 396 |
| 13 | C$_{33}$H$_{67}$ | geddic acid | 508 |
| | | Unsaturated | |
| 14 | C$_{17}$H$_{33}$ | Oleic | 282 |
| 15 | C$_{17}$H$_{31}$ | Linoleic | 280 |
| 16 | C$_{17}$H$_{29}$ | Linolenic | 278 |
| 17 | C$_{15}$H$_{29}$ | Palmitoleic | 254 |
| 18 | C$_{13}$H$_{25}$ | Myristicoleic | 226 |
| 19 | C$_{21}$H$_{41}$ | Erucic | 338 |

Fatty Alcohols Names

Fatty alcohols are useful as raw materials in the synthesis of the compounds of the present invention are commercially available from a variety of sources including BASF. They conform to the following structure;

R—OH

| Example | Formula | Name | Molecular Weight |
|---|---|---|---|
| 20 | C$_8$H$_{18}$O | 1-Capryl | 130.0 |
| 21 | C$_9$H$_{20}$O | 1-Nonanol | 144.3 |
| 22 | C$_{10}$H$_{22}$O | 1-Decanol | 158.3 |
| 23 | C$_{11}$H$_{24}$O | Undecanol | 172.3 |
| 24 | C$_{12}$H$_{26}$O | Dodecanol | 186.3 |
| 25 | C$_{18}$H$_{38}$O | Stearyl | 270.5 |
| 26 | C$_{22}$H$_{46}$O | Behenyl | 326.6 |

Example 27

Dimer Acid

Dimer acid is an item of commerce available commercially from Cognis Corporation. It conforms to the following structure:

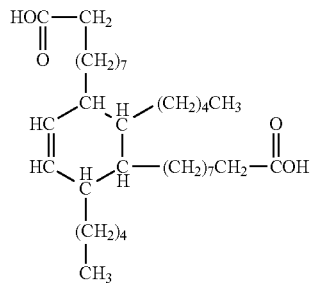

Example 28

Hydrogenated Dimer Acid

Hydrogenated dimer acid is an item of commerce available commercially from Henkel Corporation. It conforms to the following structure:

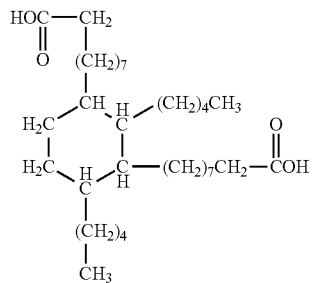

Dicarboxylic Acid

Dicarboxylic acid useful as raw materials in the synthesis of the compounds of the present invention are commercially available from a variety of sources including Cognis. They conform to the following structure;

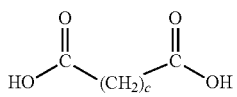

wherein;
c is an integer ranging from 1 to 10.

| Saturated Dicarboxylic acids | | | |
|---|---|---|---|
| Example | Common Name | c | Molecular Weight |
| 29 | Malonic | 1 | 104 |
| 30 | Succinic | 2 | 118 |
| 31 | Glutaric | 3 | 132 |
| 32 | Adipic | 4 | 146 |
| 33 | Pimelic | 5 | 160 |
| 34 | Subric | 6 | 174 |
| 35 | Azelaic | 7 | 188 |
| 36 | Sebacic | 8 | 202 |
| 37 | Undecanedioic | 9 | 216 |
| 38 | Dodecanedioic | 10 | 230 |

Guerbet Alcohols

Guerbet alcohols useful as raw materials in the preparation of compounds of the present invention are commercially available from a variety of sources including Sasol North America Incorporated of Houston Tex.

The structures are well known to those skilled in the art.

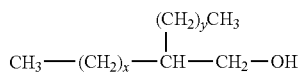

y is an integer ranging from 3-15
and x is an integer ranging from 5-17.

| Example | Y | X |
|---|---|---|
| 39 | 15 | 17 |
| 40 | 13 | 11 |
| 41 | 9 | 7 |

Ethylene Polymeric Alcohol's

Polymeric ethylene alcohols are sold under the tradename UNILIN™ alcohols. Unilin is a trademark of Baker Hughes Incorporated.

Baker Hughes defines the alcohols as "based on proprietary technology, UNILIN™ Alcohols are fully saturated, long chain, linear primary alcohols. Compared to other commercially available synthetic alcohols, UNILIN Alcohols are of higher molecular weight, greater crystallinity, and higher purity with an 80% primary alcohol concentration."

These linear alcohols are traditionally limited to C30 and lower, while UNILIN Alcohols are available with average carbon chain lengths up to C50. A further attractive feature of the UNILIN Alcohols is the relatively narrow of about 1.1 polydispersity (Mw/Mn).

$CH_3(CH_2)_d$—OH

| Example | Formula* | Trade Name | d value | Molecular Weight** |
|---|---|---|---|---|
| 42 | $C_{30}H_{61}O$ | Unilin 350 | 29 | 437 |
| 43 | $C_{39}H_{79}O$ | Unilin 425 | 38 | 563 |
| 44 | $C_{47}H_{95}O$ | Unilin 550 | 46 | 675 |
| 45 | $C_{60}H_{121}O$ | Unilin 700 | 59 | 857 |

*Calculated value
**Measured

The molecular weight is calculated from the hydroxyl value and the R-value from the molecular weight. The Tradename is not given merely for reference.

Diols

Diols are useful as raw materials in the synthesis of the compounds of the present invention are commercially available from a variety of sources including BASF. They conform to the following structure;

$HO(CH_2)_xOH$ wherein;
x is an integer ranging from 3 to 12.

| Example | Formula | Name | Molecular Weight |
|---|---|---|---|
| 45 | $HO(CH_2)_3OH$ | 1,3-Propanediol | 74.0 |
| 46 | $HO(CH_2)_{10}OH$ | 1,10-Decandiol | 174.3 |
| 47 | $HO(CH_2)_{12}OH$ | 1,12-Dodecanediol | 202.3 |

Glycerin

Glycerin is an item of commerce and is available from a variety of sources including Cognis of Cincinnati Ohio. It conforms to the following structure:

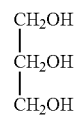

Glycerin is propane-1,2,3-triol and has a CAS number of 56-81-5.

General Procedure

Polymerization

A specified number of grams glycerin is added to a specified amount of fatty acids (examples 1-19), dicarboxylic acid (examples 29-38 and examples 27 & 28), and alcohol (examples 39-45 and examples 20-26). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

| | Diol (R$^1$) | | Chain Terminator (R$^2$) | | Diacid (R$^3$) | | Internal Fatty (R$^4$) | | Glycerin |
|---|---|---|---|---|---|---|---|---|---|
| Example | Example | Grams | Example | Grams | Example | Grams | Grams | Example | Grams |
| 48 | 45 | 0.0 | 26 | 16.4 | 28 | 167.0 | 2 | 43.4 | 23.2 |
| 49 | 45 | 0.0 | 26 | 29.2 | 28 | 161.7 | 2 | 38.5 | 20.6 |
| 50 | 45 | 0.0 | 40 | 20.3 | 28 | 164.2 | 2 | 42.6 | 22.8 |
| 51 | 45 | 0.0 | 40 | 35.6 | 28 | 157.0 | 2 | 37.4 | 20.0 |
| 52 | 45 | 10.3 | 26 | 18.2 | 28 | 184.7 | 2 | 24.0 | 12.8 |

-continued

| Example | Diol (R$^1$) Example | Grams | Chain Terminator (R$^2$) Example | Grams | Diacid (R$^3$) Example | Grams | Internal Fatty (R$^4$) Grams | Example | Glycerin Grams |
|---|---|---|---|---|---|---|---|---|---|
| 53 | 45 | 5.9 | 26 | 17.4 | 28 | 177.2 | 2 | 32.2 | 17.2 |
| 54 | 46 | 49.9 | 22 | 18.1 | 30 | 74.3 | 8 | 81.3 | 26.4 |
| 55 | 46 | 27.4 | 22 | 16.6 | 30 | 68.0 | 8 | 104.2 | 33.8 |
| 56 | 47 | 46.0 | 25 | 24.6 | 35 | 94.0 | 7 | 64.5 | 20.9 |
| 57 | 47 | 25.9 | 25 | 23.1 | 35 | 88.4 | 7 | 85.0 | 27.6 |
| 58 | 45 | 16.4 | 41 | 26.3 | 38 | 111.8 | 10 | 75.1 | 20.4 |
| 59 | 45 | 8.7 | 41 | 23.4 | 38 | 99.3 | 10 | 93.4 | 25.3 |
| 60 | 46 | 19.7 | 45 | 38.8 | 27 | 149.3 | 14 | 31.9 | 10.4 |
| 61 | 46 | 11.4 | 45 | 37.4 | 27 | 144.0 | 14 | 43.1 | 14.1 |
| 62 | 45 | 7.1 | 26 | 31.3 | 28 | 173.5 | 2 | 24.8 | 13.3 |
| 63 | 45 | 0.0 | 41 | 24.2 | 28 | 146.2 | 9 | 60.9 | 18.7 |

Applications Examples

The nature of the terminal groups surprisingly has a major impact upon the physical properties of the polymer. When R$^2$ is alkyl C28-48 (Unlin alcohol derived) the polymers are high melting, hard waxes. Alkyl products between 18 and 26 carbon atoms result in a product that is soft and exhibits thixotropic properties. This makes these materials good for pigmented products, where they allow for spreading of the pigment on the skin and skin conditioning. When the terminal group has between 8 and 16 carbon atoms the resulting material tends to be liquid. The most interesting is when the R$^2$ group is a mixture of C28-48 and liquid C8-C14. These materials are buttery and very interesting to the cosmetic chemist for skin butters.

The nature of the R$^1$ and R$^3$ group are also critically important to the functionality of the resulting polymer. Surprisingly, dimer acid provides water proofing properties to the polymer, while the C2 to C12 materials result in polymers that do not give waterproofing properties. Waterproofing products find use in color cosmetics and sun care products.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A polyester made by the esterification reaction of:
(A) a fatty acid having the structure;

R—C(O)—OH wherein;
R is selected from the group consisting of
alkyl having 7 to 33 carbon atoms;
and
alkylene having 17 to 21 carbon atoms;
(B) a fatty alcohol having the following structure:

R'—OH wherein:
R' alkyl having 8 to 22 carbon atoms;
(C) a diacid selected from the group consisting of
(i) dimer acid;
(ii) hydrogenated dimer acid;
and
(iii) dicarboxylic acid having following structure;

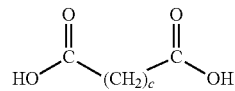

wherein;
c is an integer ranging from 1 to 10;
(D) a guerbet alcohol having the following structure;

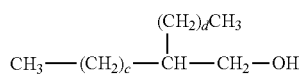

wherein;
d is an integer ranging from 3-15;
c is an integer ranging from 5-17;
(F) a diol having following structure;

HO(CH$_2$)$_x$OH wherein;
x is an integer ranging from 3 to 12;
and
(F) glycerin having the following structure:

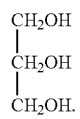

2. A polyester of claim 1 wherein R is alkyl having 7 carbon atoms.
3. A polyester of claim 1 wherein R is alkyl having 18 carbon atoms.
4. A polyester of claim 1 wherein c is 4.
5. A polyester of claim 1 wherein c is 10.
6. A polyester of claim 1 wherein x is 12.
7. A polyester of claim 1 wherein R' is alkyl having 8 carbon atoms.
8. A polyester of claim 1 wherein R' is alkyl having 12 carbon atoms.
9. A polyester of claim 1 wherein R' is alkyl having 18 carbon atoms.

10. A process for conditioning skin which comprises contacting the skin with an effective conditioning concentration of a polyester made by the esterification reaction of:
(A) a fatty acid having the structure;

R—C(O)—OH wherein;
R is selected from the group consisting of
alkyl having 7 to 33 carbon atoms;
and
alkylene having 17 to 21 carbon atoms;
(B) a fatty alcohol having the following structure:

R'—OH wherein:
R' alkyl having 8 to 22 carbon atoms;
(C) a diacid selected from the group consisting of
(i) dimer acid;
(ii) hydrogenated dimer acid;
and
(iii) dicarboxylic acid having following structure;

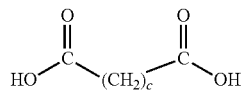

wherein;
c is an integer ranging from 1 to 10;
(D) a guerbet alcohol having the following structure;

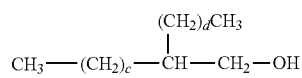

wherein;
d is an integer ranging from 3-15;
c is an integer ranging from 5-17;
(E) a diol having following structure;

$HO(CH_2)_xOH$ wherein;
x is an integer ranging from 3 to 12;
and
(F) glycerin having the following structure:

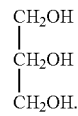

11. A process of claim 10 wherein said effective conditioning concentration ranges from 0.1 to 20% by weight.
12. A process of claim 1 wherein R is alkyl having 7 carbon atoms.
13. A process of claim 11 wherein R is alkyl having 18 carbon atoms.
14. A process of claim 11 wherein c is 4.
15. A process of claim 11 wherein c is 10.
16. A process of claim 11 wherein x is 12.
17. A process of claim 11 wherein R' is alkyl having 8 carbon atoms.
18. A process of claim 11 wherein R' is alkyl having 12 carbon atoms.
19. A process of claim 11 wherein R' is alkyl having 18 carbon atoms.

* * * * *